(12) United States Patent
Akahoshi et al.

(10) Patent No.: US 11,806,280 B2
(45) Date of Patent: Nov. 7, 2023

(54) APPARATUS FOR PHACOEMULSIFICATION

(71) Applicant: ART, LIMITED, Grand Cayman (KY)

(72) Inventors: Takayuki Akahoshi, Tokyo (JP); Ravi Nallakrishnan, Westmont, IL (US)

(73) Assignee: ART, Ltd., Grand Cayman (KY)

( * ) Notice: Subject to any disclaimer, the term of this patent is extended or adjusted under 35 U.S.C. 154(b) by 252 days.

(21) Appl. No.: 17/175,860

(22) Filed: Feb. 15, 2021

(65) Prior Publication Data

US 2021/0161710 A1 Jun. 3, 2021

Related U.S. Application Data

(63) Continuation of application No. 15/307,429, filed as application No. PCT/US2014/036510 on May 2, 2014, now Pat. No. 10,952,895.

(51) Int. Cl.
*A61F 9/007* (2006.01)

(52) U.S. Cl.
CPC ...... *A61F 9/00745* (2013.01); *A61F 9/00736* (2013.01); *A61B 2217/005* (2013.01)

(58) Field of Classification Search
CPC ............ A61F 9/00745; A61F 9/00736; A61B 2217/005
USPC .......................................................... 604/22
See application file for complete search history.

(56) References Cited

U.S. PATENT DOCUMENTS

| | | | |
|---|---|---|---|
| 2009/0137971 A1* | 5/2009 | Akahoshi | A61F 9/00763 29/428 |
| 2011/0015561 A1* | 1/2011 | Akahoshi | A61F 9/00763 604/22 |
| 2011/0201995 A1* | 8/2011 | Nallakrishnan | A61F 9/00736 604/22 |
| 2012/0157934 A1 | 6/2012 | Liao et al. | |
| 2013/0231605 A1 | 9/2013 | Walter | |
| 2013/0237993 A1 | 9/2013 | Nallakrishnan | |

FOREIGN PATENT DOCUMENTS

WO 2010/089629 A2 8/2010

* cited by examiner

*Primary Examiner* — Phillip A Gray
(74) *Attorney, Agent, or Firm* — Wood, Phillips, Katz, Clark & Mortimer (57) ABSTRACT

A phacoemulsification needle (100, 100A, 100B, 100C, 100D, 200, 200A) is provided for emulsifying body tissue. The needle (100, 100A, 100B, 100C, 100D, 200, 200A) is adapted to be attached to a phacoemulsification handpiece that imparts a vibration to the needle (100, 100A, 100B, 100C, 100D, 200, 200A). The needle (100, 100A, 100B, 100C, 100D, 200, 200A) has a body (104, 220, 220A) with a distal end (99), a proximal end (106), and an aspiration passage (124) extending between the proximal and distal ends (99, 106). The aspiration passage (124) defines a longitudinally-extending central body axis (110, 110A, 110B, 110C, 110D). The aspiration passage (124) is enlarged at the distal end (99) to define a tip (102, 102A, 102B, 102C, 102D, 210, 210A).

16 Claims, 7 Drawing Sheets

APPARATUS FOR PHACOEMULSIFICATION

CROSS-REFERENCE TO RELATED APPLICATIONS

This application is a continuation of U.S. patent application Ser. No. 15/307,429 filed Oct. 28, 2016, which is a national stage of Application No. PCT/US2014/036510 filed May 2, 2014.

FIELD OF THE INVENTION

This disclosure relates to surgical instruments used in ophthalmic surgery and, more particularly, to phacoemulsification apparatuses.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece attached to a proximal end of a hollow needle. In the handpiece, an electrical energy is applied to a piezoelectric crystal to vibrate the distal, working end of the needle at ultrasonic frequencies in order to fragment the diseased lens into small enough particles to be aspirated from the eye through an aspiration passage in the hollow needle. Commonly, an infusion sleeve is mounted around the needle at the distal end to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage may be permanent because these cells do not regenerate. Some benefits of using as small an incision as possible during such surgery are the minimization of leakage of liquid during and after surgery to help prevent tissue collapse, faster healing time, and decreased post-operative astigmatism.

Many phacoemulsification needles and tips are designed for use with handpieces that vibrate the needle longitudinally at relatively low frequencies. In addition to longitudinal vibration, certain handpieces impart a torsional motion to the needle at an oscillation frequency of about 100 cycles per second. There are also handpieces that provide torsional oscillation of the phacoemulsification tip at frequencies of about 32,000 cycles per second.

Use of the torsional-type handpiece has called for phacoemulsification needle tip designs differing from those used with the longitudinal-type handpiece. For example, needles have been designed with tips that are shaped, swaged and angled to take advantage of the needle motion created by the handpiece.

There are known phacoemulsification systems, such as the Infiniti Vision® System manufactured by Alcon Laboratories of Ft. Worth, Texas, which allow the surgeon to choose between using torsional motion, longitudinal motion, or a blend thereof with a single handpiece. Other common systems include the Sovereign® System, Whitestar Signature® System, Signature Ellips® FX System manufactured by Abbott Laboratories of Abbott Park, Illinois and the Stellaris® System manufactured by Bausch & Lomb of Rochester, NY Common frequencies for longitudinal oscillation range from 29 Hz to 43 Hz. Common frequencies for torsional oscillation range from 31 Hz to 38 Hz. A common blended setting uses torsional motion two-thirds of the time, and longitudinal motion one-third of the time. It is believed that the "blended" motion produces a more three-dimensional effect because of the back-and-forth motion imparted during longitudinal phacoemulsification and the eccentric motion produced at the tip during torsional phacoemulsification.

Many surgeons favor phacoemulsification needles having the straight tip design commonly used with longitudinal handpieces. The great majority of surgeons use longitudinal handpieces rather than the torsional handpieces, often because torsional phacoemulsification equipment is more expensive than longitudinal equipment, and thus these surgeons find themselves unable to take advantage of the enhanced phacoemulsification results claimed by the torsional phacoemulsification systems.

SUMMARY OF THE INVENTION

The inventors herein have found that forming a needle tip in an off-axis position relative to the axis of the aspiration passage extending through the needle body causes eccentric motion or "wobble" during torsional phacoemulsification and improves the efficiency of phacoemulsification while retaining the straight-tip configuration. Surprisingly, the inventors have also found that forming the tip in such an off-axis position also increases the efficiency of phacoemulsification when using a longitudinal handpiece. Preliminary clinical examinations indicate that using an off-axis needle with a longitudinal handpiece may be more efficient than using the same needle with a torsional hand piece providing 100% torsional action, where efficiency is measured by the energy dissipated during phacoemulsification. When used herein, the term "dissipated energy" refers to the amount of energy, most commonly measured in joules, used by the handpiece during phacoemulsification. Lower dissipated energy readings mean that less heat is being produced during phacoemulsification, which in turn lowers the possibility of thermal damage to the delicate eye tissues.

Use of an off-axis tip with a longitudinal hand piece appears to create a hybrid type of phacoemulsification motion without using the more complex and expensive torsional phacoemulsification apparatus. The inventors have also determined that the eccentric or wobble type of motion can be imparted to a phacoemulsification needle with no flare at the tip by forming the central aspiration passage within the needle body in an off-axis position. It is also expected that similar results will be obtained using a straight phacoemulsification needle having an aspiration passage that is formed with a cross-sectional configuration different than the cross-sectional configuration of the needle body itself, and that these results will be further amplified if the passage is also placed off-axis.

Some interior surfaces of a needle tip may result in unwanted bounce-back or ejection of tissue particles from the opening of the aspiration passage in the needle body instead of being aspirated through the aspiration passage and transported through the needle body. Such bounce-back decreases the efficiency of the overall aspiration of the needle and may increase the time of surgery. The inventors have found that providing a controlled, sloping surface in the needle tip, which extends to the aspiration passage of the needle body, can improve the aspiration capability of the needle. Different sloping configurations disclosed herein may reduce and control the bounce-back or ejection of tissue particles.

Furthermore, the inventors have found that texturizing both the needle tip surface and the surface of the sleeve can increase the surface area of the tip and sleeve surfaces to improve one or more of the efficiency of the surgery, aspiration time, and provide polishing of the capsule.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as described and claimed herein.

In accordance with one preferred embodiment of the present invention, a phacoemulsification needle is provided for emulsifying body tissue. The needle is adapted to be attached to a phacoemulsification handpiece imparting a vibration to the needle. The needle has body with a distal end, a proximal end, and an aspiration passage extending between the proximal and distal ends. The aspiration passage defines a longitudinally-extending central body axis. The needle body has a mounting portion formed at the proximal end for mounting the needle body to a phacoemulsification handpiece. The aspiration passage is enlarged at the distal end to define a tip. The tip has a radially offset portion with an interior sloping surface that slopes radially inward in a direction along the body axis toward the body proximal end.

In accordance with another preferred embodiment of the present invention, a phacoemulsification sleeve is provided. The sleeve is adapted to be attached to a phacoemulsification needle. The sleeve has a body with a distal end, a proximal end, and a through passage extending between the proximal and distal ends for receiving a needle. The sleeve body has at least one aperture for permitting flow of a fluid therethrough. The sleeve body has a textured exterior surface.

DETAILED DESCRIPTION OF THE PREFERRED EMBODIMENT

Figure 1:
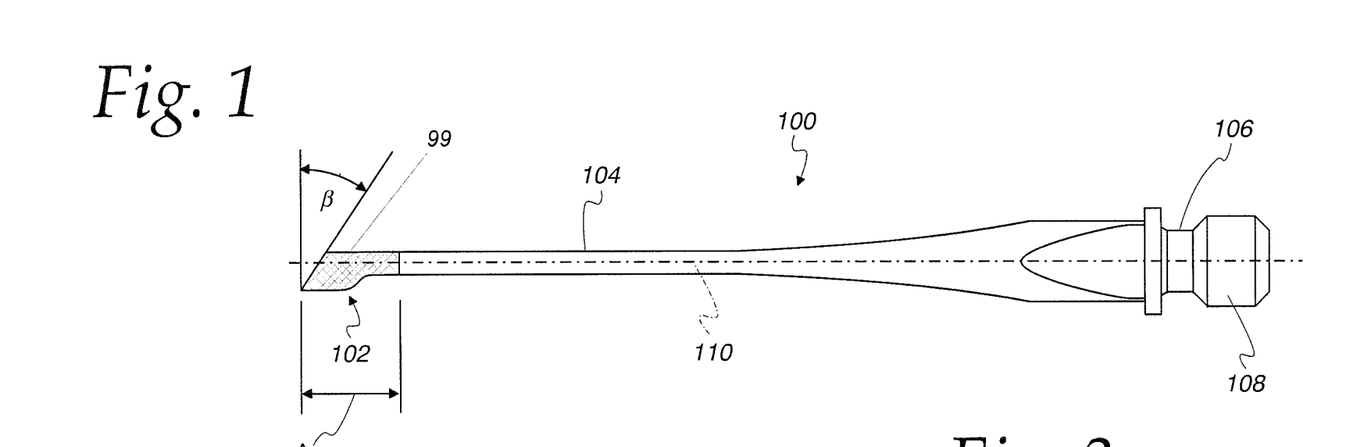
FIG. 1 is a side elevation view of a first embodiment of a phacoemulsification needle embodying the present invention.
Figure 2:
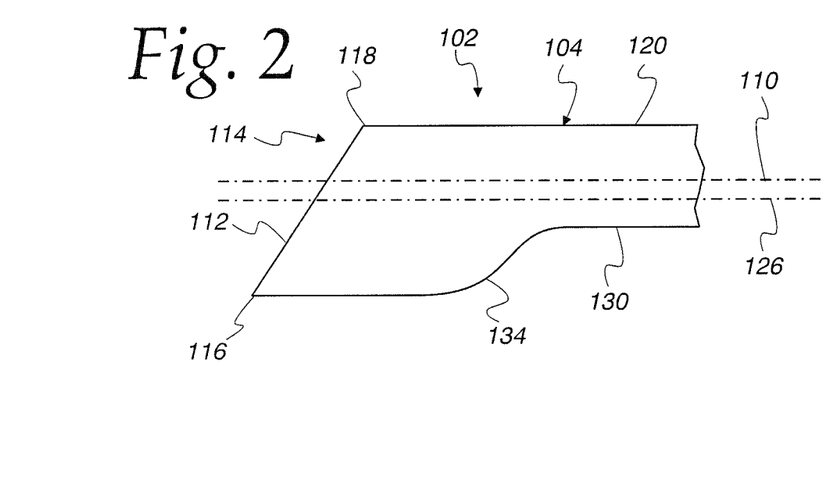
FIG. 2 is an enlarged view of the tip of the needle illustrated in FIG. 1.

Referring now to FIG. 1, the numeral 100 indicates a first preferred embodiment of a phacoemulsification needle embodying the present invention. Needle 100 is generally straight and has a needle body 104. The body has an operative or distal end 99 and a proximal end 106, defining a length of the needle body 104. The needle distal end 99 has a tip 102. The tip 102 preferably has a leading and trailing edge defined by an angle beta that is about 30 degrees to the plane running perpendicular to the length of the needle body 104. The tip 102 need not be angled at all or may be defined by other angles. FIG. 2 further illustrates that the exterior surface "A" of the needle tip 102 is preferably textured. The texture of the needle tip 102 will be discussed in detail hereinafter.

Figure 18:
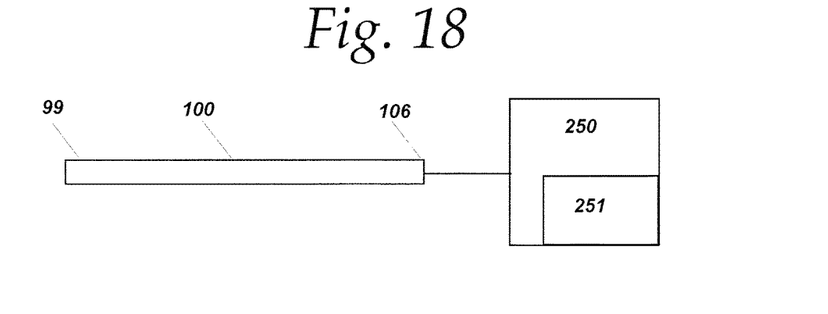
FIG. 18 is a simplified diagrammatic view of a phacoemulsification needle of FIG. 1 connected to a vibratory handpiece.

Still referring to FIG. 1, the needle proximal end 106 may have a mounting portion or mating surfaces for connecting the needle 100 to a phacoemulsification handpiece (illustrated in FIG. 18 only). The needle 100 may be connected to the handpiece in any manner such as by mating threads, clamping, friction fit, or adjustable fit. The needle body has an aspiration passage (124 in FIG. 2) running from the proximal end 106 to the distal end 99 and defining a central needle axis 110. As described hereinafter, directions inward or outward from the needle axis 110 are termed "radial" and directions along the axis 110 are either toward the distal end 99 or the proximal end 106.

Referring now to FIG. 2, which is an enlarged view of the needle tip 102. The tip 102 can generally be characterized as having a flaring shape in which the aspiration passage 124 is radially widened at the needle body distal end 99 when compared to the radial height of the aspiration passage 124 in the remaining portion of the needle body 104. The tip 102 may be characterized as having an open or hollow mouth 112 terminating in a lip 114. As previously discussed, the tip 102 may have a leading edge 116 and a trailing edge 118. The trailing edge 118 is preferably contiguous with the upper needle surface 120, while the leading edge 116 is laterally offset from the lower needle surface 130. However, in the broadest aspect of the invention, the tip 102 need not have any discernible leading or trailing edges, and the location of the leading and trailing edges may be positioned elsewhere along the lip 114.

Figure 3:
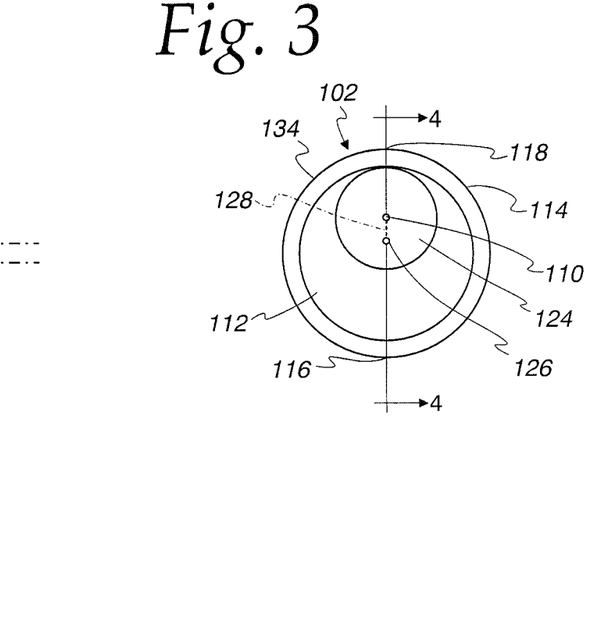
FIG. 3 is an front elevation view of the needle tip illustrated in FIG. 1.

Referring to FIG. 3, the tip 102 may have a central tip axis 126 that is offset from the needle body axis 110 by a distance 128. The aspiration passage 124 can be seen to connect to lip 114 via the open mouth 112. The first illustrated embodiment of the needle tip 102 can be seen to have a circular lip 114. Orientation of the tip axis 126 to be offset from the body axis 110 may provide beneficial eccentric motion to the phacoemulsification needle distal end 99 during vibratory oscillation (longitudinal, torsional, or a blend thereof) by the handpiece (illustrated in FIG. 18 only).

Figure 4:
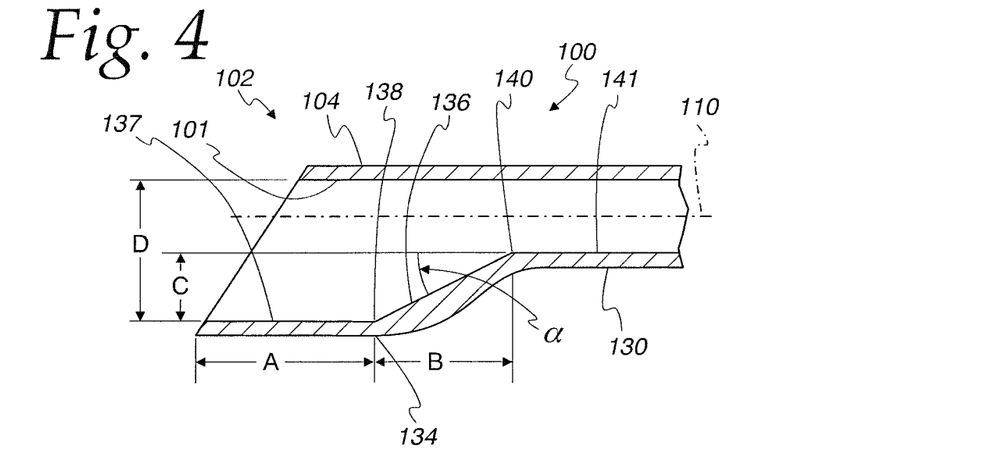
FIG. 4 is a cross-sectional view taken along plane 4-4 in FIG. 3 of the needle illustrated in FIG. 1.

Referring next to FIG. 4, which is a cross-sectional view taken along plane 4-4 of FIG. 3, the interior features of the needle distal end 99 and the needle tip 102 can be seen in detail. The first illustrated embodiment of the needle 100 shows that the tip 102 has an upper surface 103 that is coextensive with the upper surface of the aspiration passage in the needle body 104. An offset portion 134 of the needle tip 102 can be seen to extend radially outwardly from body axis 110 further than the remaining portion of the tip 102. A sloping surface 136 connects to an opening 140 of the aspiration passage that is coextensive with a lower surface 141 of the aspiration passage. The sloping surface 136 extends radially outward in the direction moving toward the open end of the tip 102 in a substantially straight surface defined by angle alpha. Angle alpha is the angle of sloping surface 136 with respect to the body axis 110. Angle alpha is less than 90 degrees, and may be between 12 degrees to 90 degrees. Preferably the slope of surface 136, or angle alpha, of is less than or equal to 45 degrees. The sloping surface 136 further connects to a second interior surface 137 at a point 138, with second interior surface 137 being generally parallel to body axis 110. Dimension "A" is the length, along the body axis 110, of the second interior surface 137. Dimension "B" is the length component, along the body axis 110, of the sloping surface 136, while dimension "C" is the height component of the sloping surface 136. In the preferred embodiment, dimension "A" is greater than that of dimension "B". Dimension "D" is the total height of the aspiration passage 124 at the needle distal end 99. In the first illustrated preferred embodiment of the needle 100, the tip 102 height "C" of the sloping surface 136 is at least one half of the total aspiration passage height "D".

The sloping surface 136 is preferably manufactured in a secondary step of milling the needle tip 102. However, the sloping surface 136 may be created by other common manufacturing methods, such as being integrally formed in the needle body, or removed by etching, electrical discharge machining, or other material removal operations.

Figure 5:
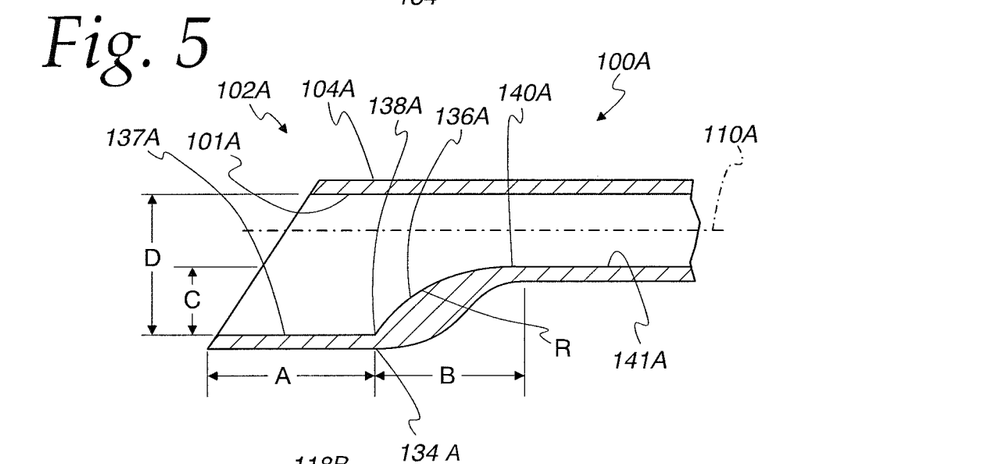
FIG. 5 is a cross-sectional view of a needle tip of a second embodiment of a phacoemulsification needle embodying the present invention.

FIG. 5 illustrates a second embodiment of a phacoemulsification needle 100A that differs only from the first embodiment 100 in that the second embodiment 100A has a sloping surface 136A in the form of a curve, when viewed in cross-section. Sloping surface 136A connects between the aspiration passage opening 140A and the second interior surface 137A. The curved sloping surface 136A is defined by a radius "R" and forms a conoid shape in three dimensions, while forming a convex curve in two dimensions. The radius "R" of the sloping surface 136A is preferably between 0.35 to 0.9 mm. This conoid shape of the sloping surface 136A may reduce the amount of removed tissue material that is deflected from the sloping surface 136A and thus improving the efficiency of the aspiration of the needle 100A in needle where the body has a radially offset portion 134A.

Figure 6:
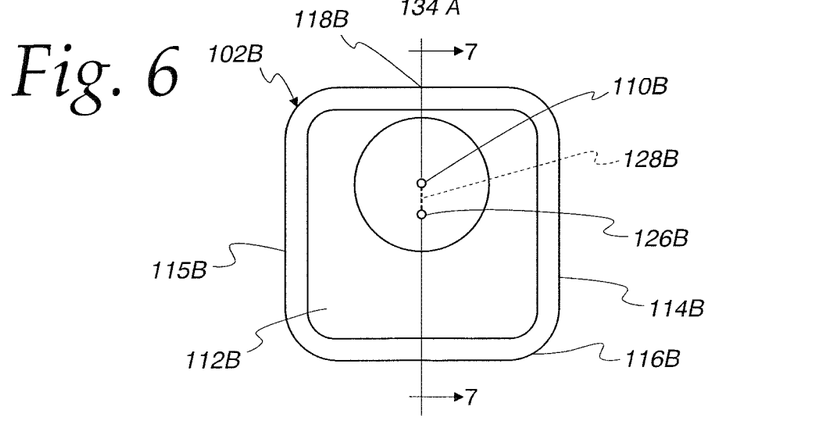
FIG. 6 is an front elevation view of a tip of a third embodiment of a phacoemulsification needle embodying the present invention.
Figure 7:
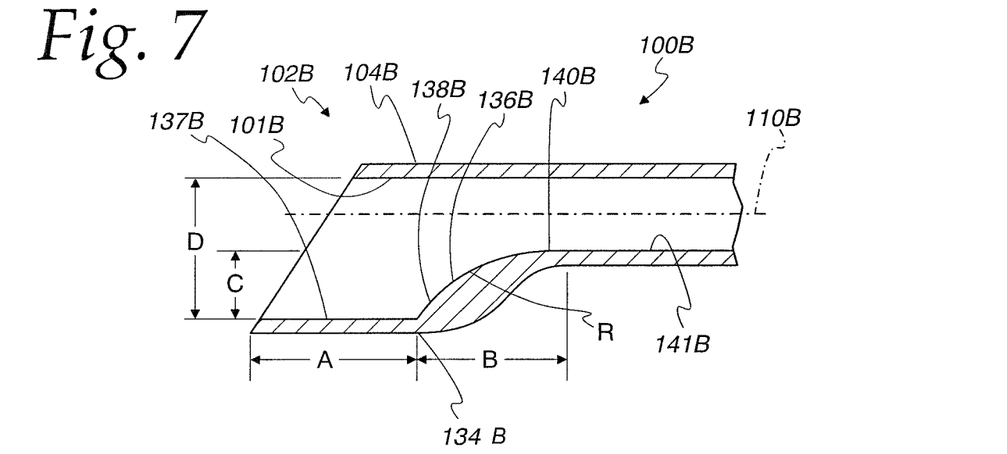
FIG. 7 is a cross-sectional view taken along plane 7-7 in FIG. 6 of the third embodiment of a needle illustrated in FIG. 6.

FIG. 6 illustrates a third embodiment of a phacoemulsification needle 100B that differs only from the second embodiment 100A in that the third embodiment 100B has a lip 114B that is generally square in shape. Tip 102B has a lip 114B with two side edges 115B, an upper edge 118B, and a lower edge 116B. As can be seen in FIG. 7, the third embodiment of the needle 110B has a sloping surface 136B in the form of a curve defined by a radius "R". The radius "R" of the sloping surface 136B is preferably between 0.35 to 0.9 mm.

Figure 8:
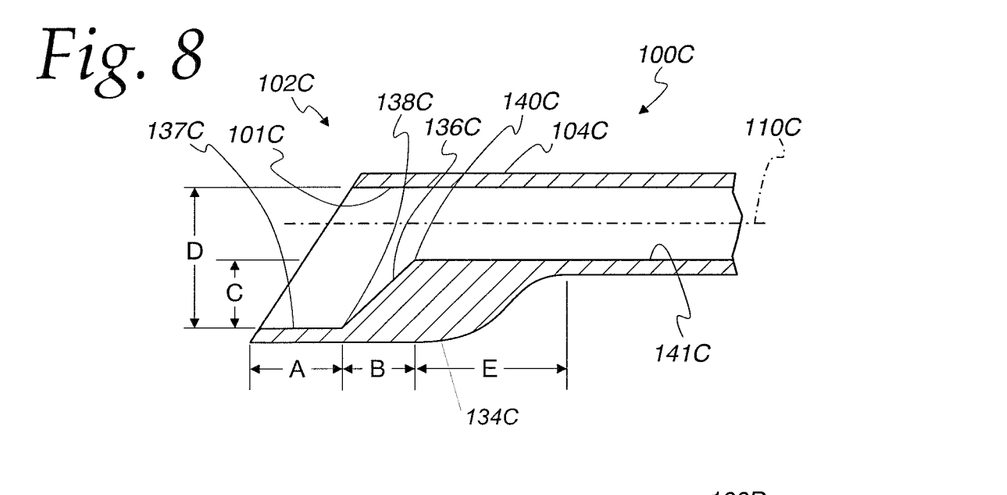
FIG. 8 is a cross-sectional view of a fourth embodiment of a tip of a phacoemulsification needle embodying the present invention.

FIG. 8 illustrates a fourth embodiment of a phacoemulsification needle 100C that differs only from the first embodiment 100 in that the fourth embodiment 100C has an elongate radially offset portion 134C defined by dimension "E", generally along the needle body axis 110C. The elongate offset portion of needle 100C has a radially outward portion of the needle tip 102C that begins to diverge radially away from the axis 110C at a position axially inward of the at point 140C. Preferably, the axial dimension "E" is greater than either of the axial dimensions "A" or "B" of the needle tip 102C. The elongate radially offset portion 134C of the needle 100C increases the non-uniform distribution of the mass in the tip 102C. It will be apparent that sloping surface 136C may be straight or curved to form a conoid shape in three dimensions.

Figure 9:
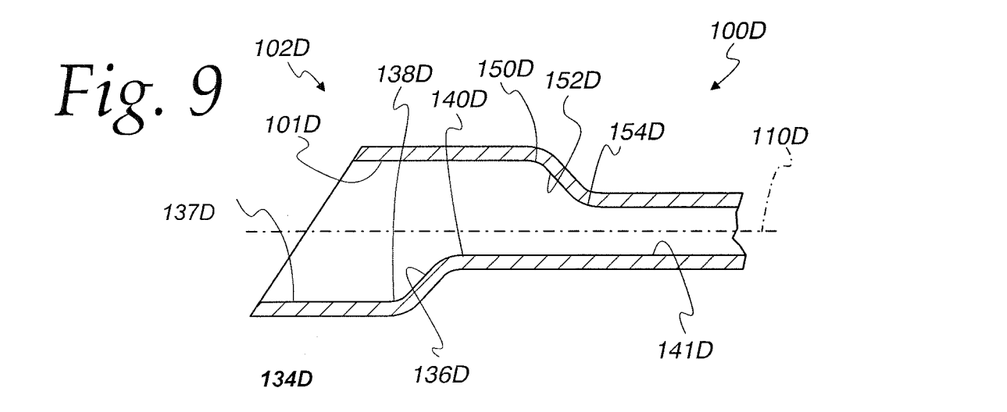
FIG. 9 is a cross-sectional view of a fifth embodiment of a tip of a phacoemulsification needle embodying the present invention.

FIG. 9 illustrates a fifth embodiment of a phacoemulsification needle 100D that differs only from the first embodiment 100 in that the fifth embodiment of the needle 100D has second radially offset portion 150D opposing a first radially offset portion 138D of the needle tip 102D. Both first radially offset portion 138D and second radially offset portion 150D are offset radially outward of the body axis 110D when compared to the remainder of the needle body 104. The second radially offset portion 150D of tip 102D extends radially outward at a point 154D of the aspiration passage 141D. Point 154D is axially inward, in the direction away from the open end of the tip 102D, of point 140D of the aspiration passage 141D where the first radially offset portion 138D extends radially outward from the needle body 104. In the illustrated fifth embodiment of the needle 100D, the second radially offset portion 150D opposes the first radially offset portion 138D, however in the broad aspects of the invention, the first and second radially offset portions need not be opposing and there may be more than just two radially offset portions in the needle distal end. Furthermore, the tip 102D may have a generally circular cross-section, square cross-section, or other polygonal or irregular cross-ssection (not illustrated). The second radially offset portion 150D of the needle 100D may increase the non-uniform distribution of the mass in the tip 102D and may improve aspiration by further widening the total surface area of the aspiration passage.

Figure 10:
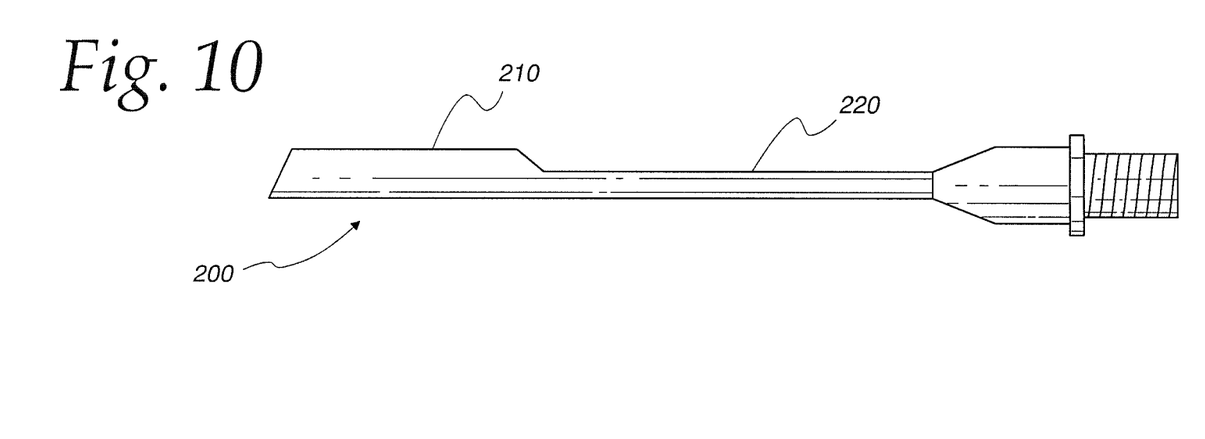
FIG. 10 is a side elevation view of a sixth embodiment of a phacoemulsification needle embodying the present invention.
Figure 11:
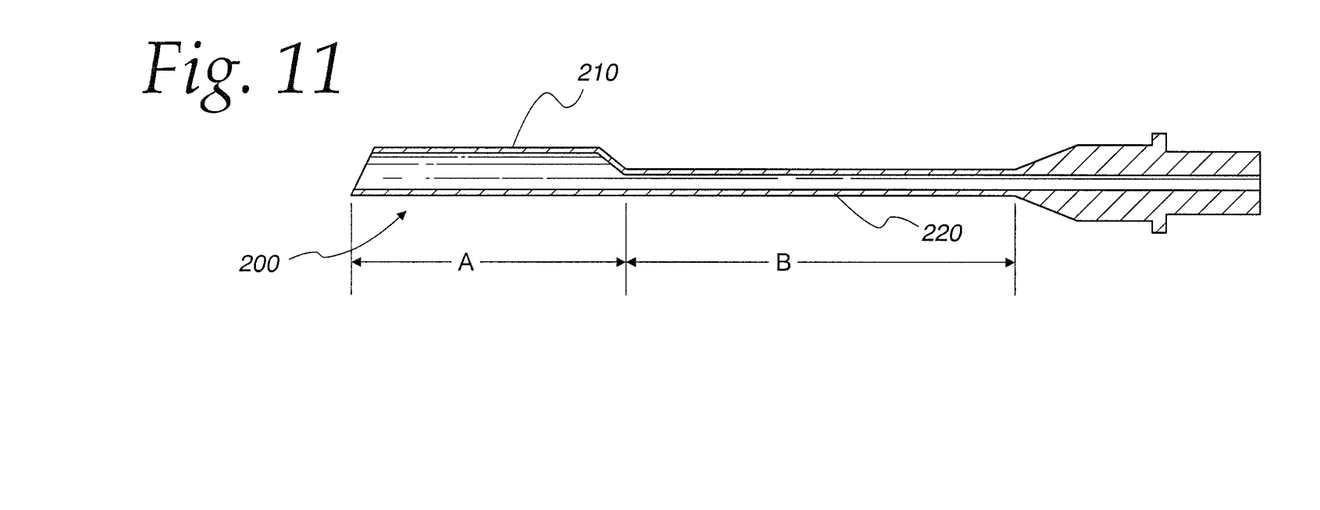
FIG. 11 is a cross-sectional view of the needle illustrated in FIG. 10, the cross-section taken along a plane running through the body axis of the needle.

FIGS. 10 and 11 illustrate a sixth embodiment of a phacoemulsification needle 200 that differs only from the first embodiment 100 in that the sixth embodiment 100 has an elongated offset tip 210. Preferably the elongate tip 210 extends an axial length "A" that is at least one half of the axial length "B" of needle body 220. Furthermore, the tip 200 may have a generally circular cross-section, square cross-section, or other polygonal or irregular cross-section (not illustrated). The elongate offset portion of the needle 200 increases the non-uniform distribution of the mass in the tip 210 and may improve aspiration by widening the area of the aspiration passage opening.

Figure 12:
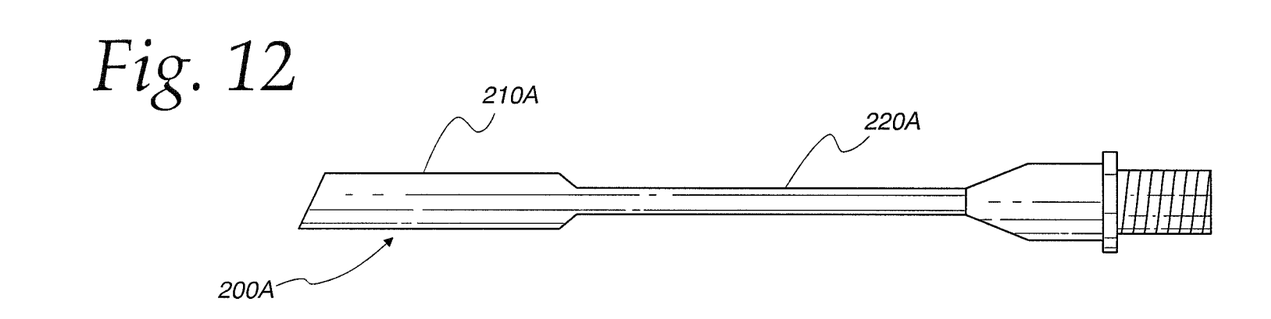
FIG. 12 is a side elevation view of a seventh embodiment of a phacoemulsification needle embodying the present invention.
Figure 13:
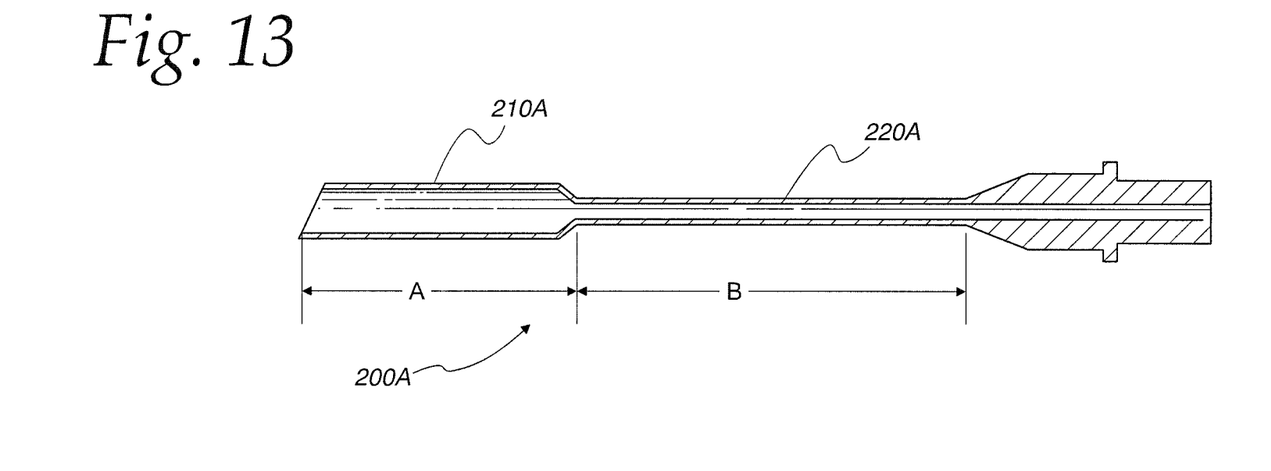
FIG. 13 is a cross-sectional view of the needle illustrated in FIG. 12, the cross-section taken along a plane running through the body axis of the needle.

FIGS. 12 and 13 illustrate a seventh embodiment of a phacoemulsification needle 200A that differs only from the sixth embodiment 200 in that the seventh embodiment 200A has an elongated offset tip 210A with two portions offset radially outward of the needle body 220A. Preferably the elongate tip 210A extends an axial length "A" that is at least one half of the axial length "B" of needle body 220A. Furthermore, the tip 200A may have a generally circular cross-section, square cross-section, or other polygonal or irregular cross-section (not illustrated). The elongate radially offset portion of the needle 200A increases the non-uniform distribution of the mass in the tip 210A and may improve aspiration by widening the surface area of the aspiration passage opening.

Figure 14:
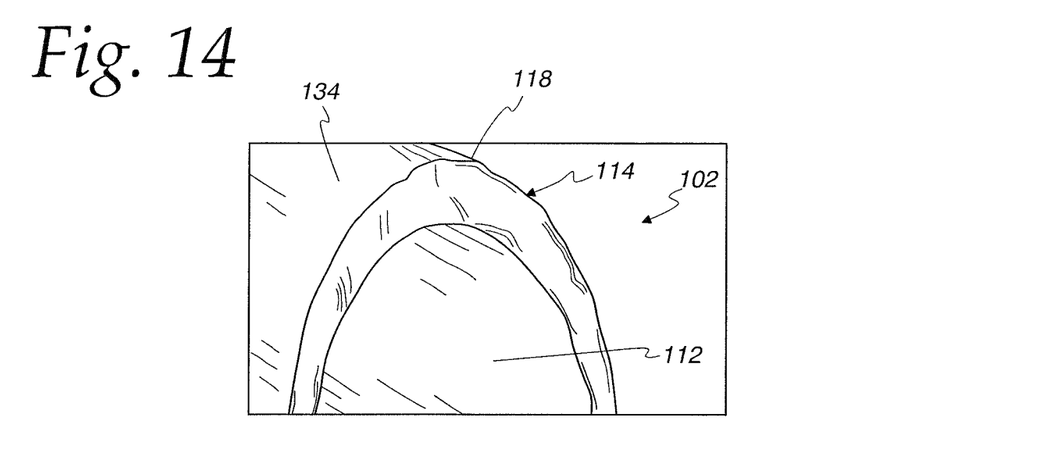
FIG. 14 is an enlarged, perspective view of the tip of the needle illustrated in FIG. 1.
Figure 15:
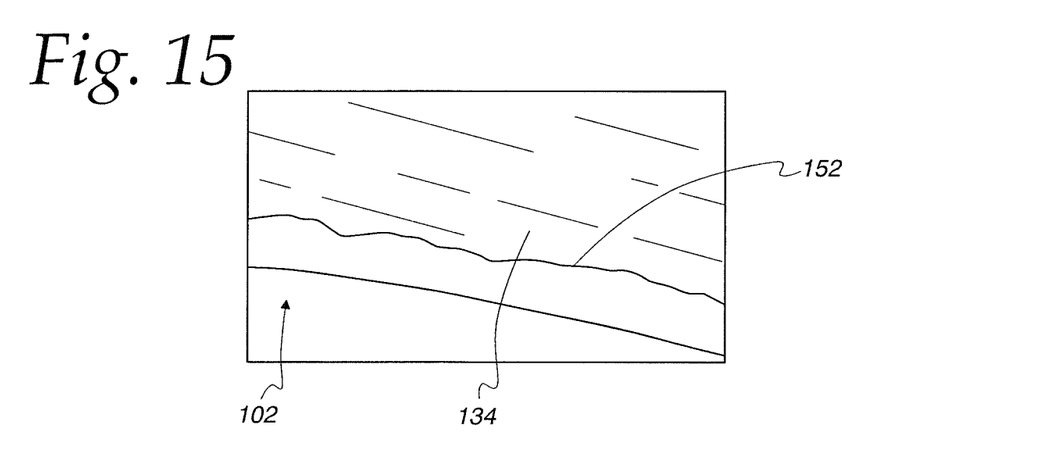
FIG. 15 is an enlarged detail view of the exterior surface of the needle tip illustrated in FIG. 14.
Figure 16:
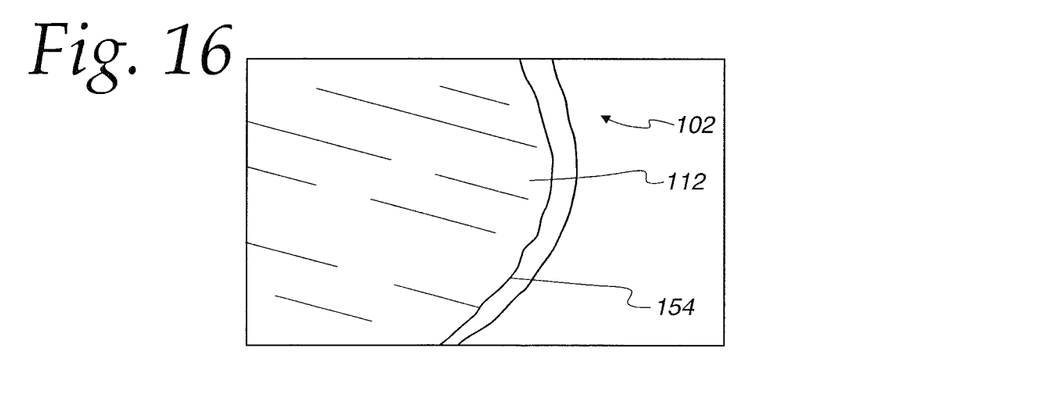
FIG. 16 is an enlarged detail view of the interior surface of the needle tip illustrated in FIG. 14.

FIGS. 14, 15, and 16 contain detailed illustrations of the tip 102 of the first embodiment of the needle 100. The safety and efficiency of phacoemulsification tips embodying the foregoing aspects of the inventive needles may be enhanced when the inner surface 152 and/or outer surface 154 of the phacoemulsification tip 102 are textured, as by tumbling, sandblasting, or other surface treatment method. Surfaces that have undergone this texturizing process appear to be pitted to create a much larger surface area for contact with tissue to be removed by phacoemulsification. The textured surface of the needle tip 102, preferably on the order of between Ra 0.2 to 0.8, is believed to increase the efficiency of the aspiration process by disrupting adherence of the tissue to the needle tip 102.

Preferably, the lip 114 of the mouth 112 is polished to round the lip 114 and remove burrs which can damage delicate tissue in the eye, such as the posterior capsule, which may be contacted by the needle tip during the phacoemulsification operation. The lip 114 may be polished in another manufacturing process after the surface treatment of one or more of the interior and exterior surfaces 152 and 154. Because of the relatively thin metallic material from which phacoemulsification needle tip 102 is formed, such edges that are not polished may be sharp enough to snag corneal tissue when a phacoemulsification needle is inserted through a corneal incision. Such edges may be sharp enough to damage delicate eye tissue, such as the posterior capsule, if the needle tip 102 is brought into contact with the capsule during surgery. The aforementioned polishing process of rounding and highly polishing and smoothing the lip 114 of phacoemulsification needle tip 102 of the type described herein reduces the likelihood that delicate eye tissue will be damaged during phacoemulsification, particularly if the needle is being used with a handpiece that produces torsional or elliptical motion.

Referring next to FIG. 18, a diagrammatic view of the needle 100 is shown attached to a handpiece 250. The handpiece 250 has a vibration imparting assembly 251. The needle 100 is attached to the handpiece 250 at the proximal end 106 of the needle 100. The handpiece 250 vibrates the needle proximal end 106 and causing the operative, distal end 99 to move at the surgical site.

Figure 17:
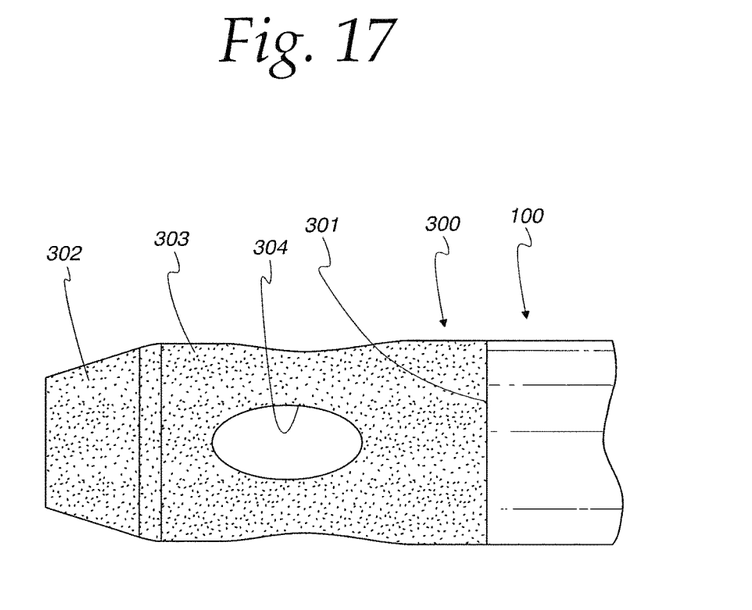
FIG. 17 is a side elevation view of a phacoemulsification sleeve installed upon the distal end of the needle illustrated in FIG. 1.

Referring finally to FIG. 17, an embodiment of an inventive phacoemulsification sleeve 300 for use with a needle 100 is illustrated. The sleeve 300 is hollow and has a proximal end 301 and a distal end 302 for being positioned proximal the distal end of the tip 102 (not visible in FIG. 17) when the needle 100 is inserted into the sleeve 300. The sleeve 300 may be made from any suitable elastomeric material such as silicone, rubber, or any hypoallergenic polymer. The sleeve has an exterior surface 303, a portion of which may be textured by electrical discharge machining of a mold cavity from which the polymeric sleeve 300 is formed. Other surface treatments may be used, such as blasting, plastically deforming the sleeve 300 or molding a secondary material to the exterior surface 303. The sleeve 300 has one or more apertures 304 for permitting fluid to flow from the interior of the sleeve 300 to the operative surface. Function of the sleeve 300 is in accordance with the operative principals disclosed in U.S. Pat. No. 7,601,135 B2. Surfaces that have undergone the texturizing process appear to be raised or pitted and may imbue the sleeve 300 with a polishing ability for polishing the capsule of the eye. The textured surface of the sleeve 300 may be on the order of 12 to 36 on the VDI scale, and is preferably about 24 on the VDI scale.

It should be understood that although the embodiments shown depict specific wall configurations of the needle and needle tip, the invention should not be so limited. Selected walls or wall portions of the phacoemulsification needle can be manufactured to various thicknesses.

The foregoing disclosure of specific embodiments is intended to be illustrative of the broad concepts comprehended by the invention.

The invention claimed is:

1. A phacoemulsification sleeve, said sleeve adapted to be attached to a phacoemulsification needle, said sleeve comprising:
    a sleeve body having an operative, distal end, a proximal end, and a through passage extending between said proximal and distal ends for receiving a phacoemulsification needle,
    said sleeve body having at least one aperture at said distal end for permitting flow of a fluid therethrough,
    said operative, distal end of said sleeve body having a textured exterior surface for polishing a capsule of an eye.

2. The phacoemulsification sleeve as recited in claim 1 wherein said textured exterior surface is integrally molded with said sleeve.

3. The phacoemulsification sleeve as recited in claim 1 wherein said textured exterior surface is between 12 to 36 on the VDI scale.

4. The phacoemulsification sleeve as recited in claim 1 wherein said textured exterior surface is 24 on the VDI scale.

5. The phacoemulsification sleeve as recited in claim 1 wherein said textured exterior surface extends from said distal end to a location proximally of said at least one aperture.

6. The phacoemulsification sleeve as recited in claim 1 wherein said textured exterior surface surrounds said at least one aperture.

7. The phacoemulsification sleeve as recited in claim 1 wherein said at least one aperture is oval.

8. The phacoemulsification sleeve as recited in claim 1 wherein said at least one aperture extends through a lateral portion of said sleeve body.

9. The phacoemulsification sleeve as recited in claim 1 wherein said textured exterior surface extends along a majority of said sleeve body.

10. The phacoemulsification sleeve as recited in claim 1 wherein distal end is tapered.

11. The phacoemulsification sleeve as recited in claim 1 further comprising:
a phacoemulsification needle received in said sleeve body, said needle adapted to be attached to a phacoemulsification handpiece for imparting a vibration to said needle, said needle having a needle body having a distal end, a proximal end, and an aspiration passage extending between said proximal and distal ends, said proximal end of said needle for mounting said needle body to a phacoemulsification handpiece, said aspiration passage having a longitudinally-extending central body axis, said aspiration passage being enlarged at said distal end to define a tip of said needle body, and
said tip of said needle body having a radially offset portion, said radially offset portion having an interior sloping surface that slopes radially inward in a direction along said body axis toward said body proximal end.

12. The phacoemulsification sleeve as recited in claim 11 wherein said interior sloping surface of said tip of said needle body is a convex curve.

13. The phacoemulsification sleeve as recited in claim 11 wherein said interior sloping surface of said tip of said needle body is substantially straight.

14. The phacoemulsification sleeve as recited in claim 13 wherein said interior sloping surface of said tip of said needle body has a slope between 12 degrees to 45 degrees.

15. The phacoemulsification sleeve as recited in claim 11 wherein said tip of said needle body has a textured surface that is at least one of:
(a) an exterior surface of said tip of said needle body; and
(b) an interior surface of said tip of said needle body.

16. The phacoemulsification sleeve as recited in claim 15 wherein said textured surface of said tip of said needle body has a surface roughness of between Ra 0.2 to 0.8.

\* \* \* \* \*